United States Patent [19]

Atwal

[11] Patent Number: 4,847,379
[45] Date of Patent: Jul. 11, 1989

[54] 3,6-DIHYDRO-1,5(2H)-PYRIMIDINECARBOXYLIC ACID ESTERS

[75] Inventor: Karnail Atwal, Cranbury, N.J.

[73] Assignee: E. R. Squibb & Sons, Inc., Princeton, N.J.

[21] Appl. No.: 126,528

[22] Filed: Nov. 30, 1987

[51] Int. Cl.$^4$ .................. C07D 239/36; C07D 401/06; C07D 401/14; C07D 417/06
[52] U.S. Cl. ............................ 544/316; 540/601; 544/58.6; 544/123; 544/295; 544/82
[58] Field of Search ............... 544/316, 58.6, 123, 544/295, 82; 514/274; 540/601

[56] References Cited
U.S. PATENT DOCUMENTS
4,728,652 3/1988 Atwal .......................... 544/316

OTHER PUBLICATIONS
Burger, Medicinal Chemistry, 1960, pp. 566, 568, 580, 600 and 601.

Primary Examiner—John M. Ford
Attorney, Agent, or Firm—Theodore R. Furman, Jr.

[57] ABSTRACT

Compounds having the formula

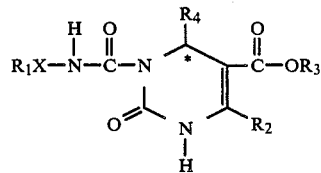

and pharmaceutically acceptable salts thereof, wherein X is oxygen or nitrogen and $R_4$ is aryl, are disclosed. These novel compounds are useful, for example, as cardiovascular agents.

6 Claims, No Drawings

3,6-DIHYDRO-1,5(2H)-PYRIMIDINECARBOXYLIC ACID ESTERS

SUMMARY OF THE INVENTION

Compounds having the formula $$\text{R}_1\text{X}-\overset{H}{N}-\overset{O}{\overset{\|}{C}}-N\overset{R_4}{\underset{\underset{H}{N}}{\overset{*}{\underset{|}{C}}}}\overset{O}{\underset{R_2}{\overset{\|}{C}-OR_3}} \quad \text{I}$$

and pharmaceutically acceptable salts thereof, are cardiovascular agents. In formula I, and throughout the specification, the symbols are as defined below.

X is O, N-R;

R is hydrogen, alkyl, cycloalkyl, aryl, or arylalkyl and $R_1$ is hydrogen, alkyl, cycloalkyl, aryl, $$-\underset{R_6}{\overset{R_5}{\underset{|}{\overset{|}{C}}}}-(CH_2)_n-Y_2, \quad -\underset{R_6}{\overset{R_5}{\underset{|}{\overset{|}{C}}}}-(CH_2)_p-Y_3$$

or halo substituted alkyl, or R and $R_1$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azeipinyl substituted with alkyl, alkoxy, alkylthio, halo, trifluoromethyl or hydroxy;

$R_2$ is hydrogen, alkyl, alkenyl, alkynyl, cycloalkyl, aryl, $$-\underset{R_6}{\overset{R_5}{\underset{|}{\overset{|}{C}}}}-(CH_2)_n-Y_1,$$

or halo substituted alkyl;

$R_3$ is hydrogen, alkyl, cycloalkyl, aryl, $$-\underset{R_6}{\overset{R_5}{\underset{|}{\overset{|}{C}}}}-(CH_2)_n-Y_2, \quad -\underset{R_6}{\overset{R_5}{\underset{|}{\overset{|}{C}}}}-(CH_2)_p-Y_3,$$

or halo substituted alkyl;

$R_4$ is aryl;

$R_5$ and $R_6$ are each independently hydrogen, alkyl, $-(CH_2)q-$aryl or $-(CH_2)q-$cycloalkyl;

$Y_1$ is cycloalkyl, aryl, hydroxyl, alkoxy, aryl—$(CH_2)_m$—O—, mercapto, alkylthio, aryl—$(CH_2)_m$—S—, amino, substituted amino, carbamoyl, (substituted amino)

$$-\overset{O}{\overset{\|}{C}}-,$$

carboxyl, alkoxycarbonyl, $$\text{alkyl-}\overset{O}{\overset{\|}{C}}-, \quad \text{aryl-}(CH_2)_m-\overset{O}{\overset{\|}{C}}-, \quad \text{alkyl-}\overset{O}{\overset{\|}{C}}-O- \text{ or}$$

$$\text{aryl-}(CH_2)_m-\overset{O}{\overset{\|}{C}}-O-;$$

$Y_2$ is cycloalkyl, aryl, carbamoyl, (substituted amino)

$$-\overset{O}{\overset{\|}{C}}-,$$

carboxyl, alkoxycarbonyl, $$\text{alkyl-}\overset{O}{\overset{\|}{C}}-, \text{ or aryl-}(CH_2)_m-\overset{O}{\overset{\|}{C}}-;$$

$Y_3$ is hydroxyl, alkoxy, aryl-$(CH_2)_m$—O—, mercapto, alkylthio, aryl-$(CH_2)_m$—S—, $$\text{alkyl-}\overset{O}{\overset{\|}{C}}-O-, \quad \text{aryl-}(CH_2)_m-\overset{O}{\overset{\|}{C}}-O-,$$

amino, or substituted amino;

q is 0, 1, 2 or 3;
m is 0 or an integer of 1 to 6;
n is 0 or an integer of 1 to 5; and
p is an integer of 1 to 5.

DETAILED DESCRIPTION OF THE INVENTION

The compounds of formula I, and the pharmaceutically acceptable salts thereof, are cardiovascular agents. They act as calcium entry blocking vasodilators and are especially useful as antihypertensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

It is believed that the compounds of this invention, in addition to being useful as hypotensive agents, may also be useful as anti-arrhythmic agents, anti-anginal agents, anti-ischemic agents, anti-fibrillatory agents, anti-asthmatic agents, and in limiting myocardial infarction.

The compounds of this invention can also be formulated for use as hypotensive agents in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, which is preferred, pentafluoroethyl, 2,2,2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "substituted amino" refers to a group of the formula —NZ$_1$Z$_2$ wherein Z$_1$ is hydrogen, alkyl, or aryl—(CH$_2$)$_m$— and Z$_2$ is alkyl or aryl—(CH$_2$)$_m$— or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

The compounds of the formula I can be prepared by reacting a keto ester of the formula

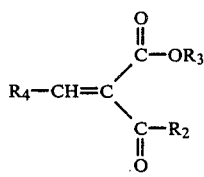

with a compound of the formula

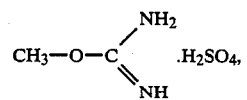

that is, O-methylisourea hydrogen sulfate, in the presence of sodium acetate or sodium bicarbonate to yield a tautomeric mixture of compounds having the formula

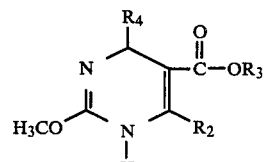

and

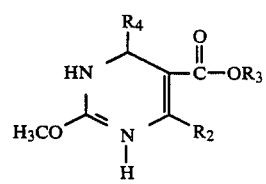

Compound IV (the mixture of (a) and (b)), in solvents, e.g. dichloromethane and pyridine, is treated with 4-nitrophenylchloroformate to provide a compound having the formula

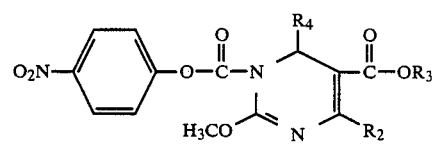

Compound V is treated with acid, e.g. hydrochloric, in a polar solvent, such as methanol and tetrahydrofuran, to provide a compound of the formula

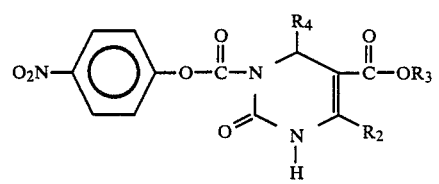

Thereafter, compound VI in a solvent, e.g. acetonitrile, can be reacted with a compound of the formula

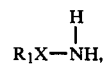

or salts thereof, in an inert atmosphere such as argon to provide the compounds of formula I.

In those instances wherein the reactants described above contain reactive substituents not meant to participate in the reaction, it may be necessary to first protect these functional groups, carry out the desired reaction, and then remove the protecting group.

The compounds of formula I contain an asymmetric center within the pyrimidine ring as represented by the *. Thus, the compounds of formula I can exist in stereoisomeric forms or in mixtures thereof. The above-described processes can utilize racemates, enantiomers or diastereomers as starting materials. When diastereomeric products are prepared, they can be separated by conventional chromatographic or fractional crystallization methods.

The compounds of formula I that contain a basic or acidic group form acid addition and basic salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g., sodium, potassium and lithium) and alkaline earth metal salts (e.g., calcium and magnesium). The salts can be obtained by reacting the product with an equivalent amount of the acid in a medium in which the salt precipitates.

Preferred compounds of this invention are those wherein:

$R_2$ is alkyl (especially methyl), $R_3$ is alkyl (especially isopropyl) and $R_4$ is 3-nitrophenyl, and R and $R_1$ are each hydrogen or one of R and $R_1$ is hydrogen and the other is benzyl.

The following examples are specific embodiments of this invention.

EXAMPLE 1

3,6-Dihydro-4-methyl-6-(3-nitrophenyl)-2-oxo-1,5(2H)-pyrimidinecarboxylic acid, 5-(1-methylethyl)ester, 1-hydrazide

A.

1,4-Dihydro-2-methoxy-6-methyl-4-(3-nitrophenyl)-5-pyrimidinecarboxylic acid, 1-methylethyl ester A reaction mixture containing
2-[3-nitrophenyl)methylene]-3-oxobutanoic acid,
1-methylethyl ester (10.0 g, 36.0 mmol), sodium bicarbonate (8.40 g, 108 mmol), and
O-methylpseudourea hydrogen sulfate (8.06 g, 46.8 mmol) in dimethylformamide (54 ml) was heated at 60° C., under argon for about 2½ days. The reaction mixture was diluted with water and extracted with ethyl acetate. The organic phase was washed with water (six times) and saturated sodium chloride, dried (potassium carbonate) and evaporated. The residue was passed through a short pad of silica gel and crystallized from isopropyl ether/hexanes to give the title compound as yellow crystals (8.04 g), m.p. 130°-132° C.

Analysis calc'd for $C_{16}H_{19}N_3O_5$: C, 57.65; H, 5.74; N, 12.61;
Found: C, 57.72; H, 5.93; N, 12.66.

B.

3,6-Dihydro-4-methyl-6-(3-nitrophenyl)-2-oxo-1,5-(2H)-pyrimidinedicarboxylic acid, 5-(1-methylethyl) 1-(4-nitrophenyl)ester The title A compound (15.5 g, 46.5 mmol) in dichloromethane (100 mL) and pyridine (20 mL) was cooled to 0° C. under argon and was treated dropwise with a solution of 4-nitrophenylchloroformate (14.9 g, 52.0 mmol) in dichloromethane (40 mL). After the addition was finished, the cooling bath was removed and the reaction was allowed to stir at room temperature for 2 hours. The solvent was removed under reduced pressure; the resulting solid was suspended in tetrahydrofuran (75 mL) and methanol (75 mL) and treated with 2.5N hydrochloric acid until pH~2.0. The reaction was allowed to stir at room overnight (became a homogeneous light yellow solution) and most of the solvent was then evaporated. The residue was diluted with water and extracted with ethyl acetate. The combined extracts were washed with water, 5% sodium carbonate and brine. After drying over anhydrous magnesium sulfate, the solvent was evaporated and the residue was passed through a short column of silica gel (10% ethyl acetate in dichloromethane). The product was crystallized from dichloromethane-isopropyl ether to provide the title B compound as a colorless solid (15.6 g). The mother liquor was concentrated and crystallized from the same solvent system to give a second crop (1.01 g) for a total of 16.61 g, m.p. 118°-120° C.

Microanalysis calc'd for $C_{22}H_{20}N_4O_9$: C, 54.54; H, 4.16; N, 11.57;
Found C, 54.24; H, 3.97; N, 11.46.

C.

3,6-Dihydro-4-methyl-6-(3-nitrophenyl)-2-oxo-1,5(2H)-pyrimidinecarboxylic acid, 5-(1-methylethyl)ester, 1-hydrazide The title B compound (2 g, 4.01 mmol) in acetonitrile (10 ml) was cooled to 0° C. under argon and was treated with anhydrous hydrazine (0.15 mL, 4.8 mmol). The reaction turned yellow instantaneously and a colorless solid precipitated out. The reaction was allowed to stir at room temperature for 45 minutes and the colorless solid was filtered off and washed with acetonitrile to provide the title compound (1.35 g). The product was recrystallized from absolute ethanol to yield the title compound (1.21 g) as a colorless solid, m.p. 205°-206° C.

Analysis calc'd for $C_{16}H_{19}N_5O_6$: C, 50.92; H, 5.07; N, 18.55;
Found: C, 51.06; H, 5.13; N, 18.48.

EXAMPLE 2

1,2,3,6-Tetrahydro-4-methyl-6-(3-nitrophenyl)-2-oxo-1-[[(phenylmethoxy)amino]-carbonyl]-5-pyrimidinecarboxylic acid, 1-methylethyl ester A mixture of the title B compound of Example 1 (2.43 g, 5.01 mmol) and sodium bicarbonate (0.50 g, 6.01 mmol) in acetonitrile (20 ml) was treated, in three portions, with 0-benzylhydroxylamine hydrochloride (0.84 g, 5.26 mmol). After 2 hours at room temperature, the reaction was diluted with chloroform (10 ml) and stirred overnight. It was then heated at 50° C. overnight (19 hours). The reaction was then evaporated and partitioned between 1 N sodium hydroxide solution and ether. The organic phase was washed twice with 1 N sodium hydroxide, twice with saturated sodium chloride, dried over anhydrous magnesium sulfate, and evaporated. The residue was crystallized from dichloromethane/-isopropanol to give colorless crystals (1.60 g). Partial evaporation of the filtrate lead to crystallization of a second crop (0.48 g). These two crops were combined and recrystallized from chloroform/isopropanol to give the title compound (1.58 g) as colorless crystals, m.p. 166°-167° C.

Analysis calc'd for $C_{23}H_{24}N_4O_7$; C, 58.97; H, 5.16; N, 11.96;
Found: C, 59.14; H, 5.14; N, 12.00.

EXAMPLES 3-23

Following the methods outlined above and the procedures described in Examples 1 and 2, the following compounds of formula I within the scope of the present invention can be prepared.

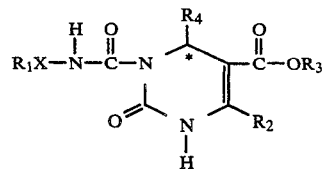

| Ex. No. | X | R | $R_1$ | $R_2$ | $R_3$ | $R_4$ |
|---|---|---|---|---|---|---|
| 3 | —N— | —H | —CH₃ | —CH₃ | —CH₃CH₂ | 2-chlorophenyl |
| 4 | —N— | —H | —CH₂—C₆H₅ | —CH₃ | —CH(CH₃)₂ | 3-chlorophenyl |
| 5 | —N— | —CH₃ | —CH₃ | —CH₃ | —CH₃CH₂ | 2,3-dichlorophenyl |
| 6 | —N— | —H | —CH₂CH₂N(pyrrolidinyl) | —CH₃ | —CH(CH₃)₂ | 2-(trifluoromethyl)phenyl |
| 7 | —N— | —H | —CH₂CH₂N(CH₃)—CH₂—C₆H₅ | —CH₃ | —CH₂CH₃ | 3-nitrophenyl |
| 8 | —N— | —CH₃ | —CH₃ | —CH₃ | —CH₂CH₂N(CH₃)—CH₂—C₆H₅ | 2-chlorophenyl |
| 9 | —N— |  | —CH₂(CH₂)₃CH₂— | —CH₃ | —CH₂CH₃ | 2-nitrophenyl |
| 10 | —N— |  | —(CH₂)₂S—(CH₂)₂— | —CH₃ | —CH₂CH₃ | 2-(trifluoromethyl)phenyl |
| 11 | —N— | —CH₃ | —CH₃ | —CH₃ | —CH₂CH₂OCH₃ | 3-nitrophenyl |

-continued

| Ex. No. | X | R | R₁ | R₂ | R₃ | R₄ |
|---|---|---|---|---|---|---|
| 12 | —N— | H | —CH₂—C₆H₅ (benzyl) | —CH₂CH₂NCH₂—C₆H₅ with N–CH₃ | —CH₂CH₃ | 2-Cl-C₆H₄ |
| 13 | —N— | H | —CH(CH₃)₂ | —CH₂CH₂OCH₂—C₆H₅ | —CH(CH₃)₂ | 3-NO₂-C₆H₄ |
| 14 | —O— |  | —CH₂—C₆H₅ | —CH₃ | —CH₂CH₃ | 2-Cl-C₆H₄ |
| 15 | —O— |  | —CH₃ | —CH₃ | —CH(CH₃)₂ | 3-NO₂-C₆H₄ |
| 16 | —O— |  | —CH(CH₃)₂ | —CH₃ | —CH₂CH₂NCH₂—C₆H₅ with N–CH₃ | 2-NO₂-C₆H₄ |
| 17 | —O— |  | —CH₂CH₂NCH₂—C₆H₅ with N–CH₃ | —CH₃ | —CH₂CH₃ | 2-CF₃-C₆H₄ |
| 18 | —O— |  | —CH₃ | —CH₂CH₂NCH₂—C₆H₅ with N–CH₃ | —CH₂CH₃ | 2,3-Cl₂-C₆H₃ |
| 19 | —O— |  | —CH₂—C₆H₅ | —CH₂CH₂OCH₃ | —CH(CH₃)₂ | 3-Cl-C₆H₄ |
| 20 | —O— |  | —CH₂CH₃ | —CH₃ | —CH₂CH₂OCH₂—C₆H₅ | 2-CF₃-C₆H₄ |
| 21 | —O— |  | —CH₂CH₂—C₆H₅ | —CH₃ | —CH₂CH₂OCH₃ | 2-Cl-C₆H₄ |
| 22 | —O— |  | —CH₂CH₂N(pyrrolidine) | —CH₃ | —CH₂CH₃ | 3-NO₂-C₆H₄ |

| Ex. No. | X | R | R₁ | R₂ | R₃ | R₄ |
|---|---|---|---|---|---|---|
| 23 | —O— | | —CH₂CH₂CH(CH₃)—CH₃ | —CH₃ | —CH₃ | 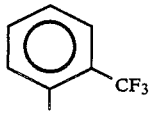 |

What is claimed is:

1. A compound having the formula

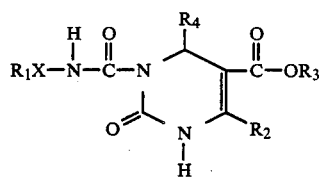

including pharmaceutically acceptable salts thereof, wherein

X is O, N-R;

R is hydrogen, alkyl, cycloalkyl, aryl, or arylalkyl and R₁ is hydrogen, alkyl, cycloalkyl, aryl,

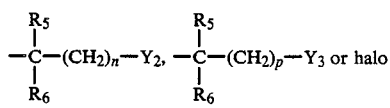

substituted alkyl, or R and R₁ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azepinyl substituted with alkyl, alkoxy, alkylthio, halo, trifluoromethyl or hydroxy;

R₂ is hydrogen, alkyl, alkenyl, alkynyl, cycloalkyl, aryl,

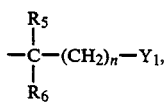

or halo substituted alkyl;

R₃ is hydrogen, alkyl, cycloalkyl, aryl,

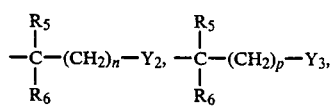

or halo substituted

R₄ is aryl;

R₅ and R₆ are each independently hydrogen, alkyl, —(CH₂)$_q$—aryl or —(CH₂)$_q$—cycloalkyl;

Y₁ is cycloalkyl, aryl, hydroxyl, alkoxy, aryl—(CH₂)$_m$—O—, mercapto, alkylthio, aryl—(CH₂)$_m$—S—, amino, substituted amino, carbamoyl, (substituted amino)

$-\overset{O}{\underset{\|}{C}}-$, carboxyl, alkoxycarbonyl, alkyl-$\overset{O}{\underset{\|}{C}}-$, aryl-(CH₂)$_m$—$\overset{O}{\underset{\|}{C}}-$, alkyl-$\overset{O}{\underset{\|}{C}}$—O— or aryl-(CH₂)$_m$—$\overset{O}{\underset{\|}{C}}$—O—;

Y₂ is cycloalkyl, aryl, carbamoyl, (substituted amino)

$-\overset{O}{\underset{\|}{C}}-$, carboxyl, alkoxycarbonyl, alkyl-$\overset{O}{\underset{\|}{C}}-$, or aryl-(CH₂)$_m$—$\overset{O}{\underset{\|}{C}}-$;

is hydroxyl, alkoxy, aryl—(CH₂)$_m$—O—, mercapto, alkylthio, aryl—(CH₂)$_m$—S—, alkyl-$\overset{O}{\underset{\|}{C}}$—O—, aryl-(CH₂)$_m$—$\overset{O}{\underset{\|}{C}}$—O—, amino, or substituted amino;

q is 0, 1, 2 or 3;

m is 0 or an integer of 1 to 6;

n is 0 or an integer of 1 to 5; and is an integer of 1 to 5; further, wherein "alkyl" and "alkoxy" refer to both straight and branched chain groups having 1 to 8 carbon atoms;

"halo substituted alkyl" refers to alkyl groups in which one or more hydrogens have been replaced by chloro, bromo or fluoro groups;

"aryl" refers to phenyl and substituted phenyl wherein the substituents are independently selected from one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;

"alkenyl" and "alkynyl" refer to both straight and branched chain groups having 2 to 8 carbon atoms;

"cycloalkyl" refers to those groups having 3, 4, 5, 6 or 7 carbon atoms;

"halo" refers to chloro, bromo, fluoro and iodo; and,

"substituted amio" refers to a group of the formula —NZ₁Z₂ wherein Z₁ is hydrogen, alkyl, or aryl—(CH₂)$_m$— and Z₂ is alkyl or aryl—(CH₂)$_m$— or Z₁ and Z₂ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

2. A compound of claim 1 wherein
R is hydrogen;
$R_1$ is hydrogen or benzyl;
$R_2$ is alkyl;
$R_3$ is alkyl; and,
$R_4$ is 3-nitrophenyl.

3. A compound of claim 1 wherein
X is nitrogen;
R is hydrogen;
$R_1$ is hydrogen;
$R_2$ is methyl;
$R_3$ is methylethyl; and,
$R_4$ is 3-nitrophenyl.

4. A compound of claim 1 wherein
X is oxygen;
R is hydrogen;
$R_1$ is benzyl;
$R_2$ is methyl;
$R_3$ is methylethyl; and,
$R_4$ is 3-nitrophenyl.

5. A compound in accordance with claim 1 having the name 3,6-dihydro-4-methyl-6-(3-nitrophenyl)-2-oxo-1,5(2H)-pyrimidinecarboxylic acid, 5-(1-methylethyl)ester, 1-hydrazide.

6. A compound in accordance with claim 1 having the name 1,2,3,6-tetrahydro-4-methyl-6-(3-nitrophenyl)-2-oxo-1-[[(phenylmethoxy)amino]-carbonyl]-5-pyrimidinecarboxylic acid, 1-methylethyl ester.

* * * * *

UNITED STATES PATENT AND TRADEMARK OFFICE
CERTIFICATE OF CORRECTION

PATENT NO. : 4,847,379

DATED : July 11, 1989

INVENTOR(S) : Karnail Atwal

It is certified that error appears in the above-identified patent and that said Letters Patent is hereby corrected as shown below:

Column 11, line 60, insert --alkyl;-- after "halo substituted";

Column 11, line 67 and Column, line 15, "(substituted amino)" and "$-\overset{\overset{O}{\|}}{C}-$," should read as --(substituted amino)$-\overset{\overset{O}{\|}}{C}-$ --;

Column 12, lines 20-24, "(substituted amino)" and "$-\overset{\overset{O}{\|}}{C}-$," should read as --(substituted amino)$-\overset{\overset{O}{\|}}{C}-$ --;

Column 12, line 40, insert --p-- before "is an integer of 1 to 5;"

UNITED STATES PATENT AND TRADEMARK OFFICE
CERTIFICATE OF CORRECTION

PATENT NO. : 4,847,379

DATED : July 11, 1989

INVENTOR(S) : Karnail Atwal

It is certified that error appears in the above-identified patent and that said Letters Patent is hereby corrected as shown below:

Column 12, line 64, "aryIalkyl-1-piperazinyl," should read as --arylalkyl-1-piperazinyl--.

Signed and Sealed this

First Day of January, 1991

Attest:

HARRY F. MANBECK, JR.

Attesting Officer

Commissioner of Patents and Trademarks